United States Patent
Fernandes et al.

(10) Patent No.: US 11,547,407 B2
(45) Date of Patent: Jan. 10, 2023

(54) STAPLE LINE REINFORCEMENT FOR SURGICAL STAPLING APPARATUS

(71) Applicant: Covidien LP, Mansfield, MA (US)

(72) Inventors: Roanit Fernandes, Hyderabad (IN); Kenneth H. Whitfield, North Haven, CT (US)

(73) Assignee: Covidien LP, Mansfield, MA (US)

( * ) Notice: Subject to any disclaimer, the term of this patent is extended or adjusted under 35 U.S.C. 154(b) by 144 days.

(21) Appl. No.: 17/177,342

(22) Filed: Feb. 17, 2021

(65) Prior Publication Data

US 2021/0290230 A1 Sep. 23, 2021

Related U.S. Application Data

(60) Provisional application No. 62/991,655, filed on Mar. 19, 2020.

(51) Int. Cl.
*A61B 17/072* (2006.01)
*A61B 17/00* (2006.01)

(52) U.S. Cl.
CPC .. *A61B 17/07207* (2013.01); *A61B 17/07292* (2013.01); *A61B 2017/0053* (2013.01); *A61B 2017/07257* (2013.01); *A61B 2017/07271* (2013.01)

(58) Field of Classification Search
CPC .................. A61B 17/07207; A61B 17/07292
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 3,364,200 A | 1/1968 | Ashton et al. | |
| 3,499,591 A | 3/1970 | Green | |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Australian Examination Report No. 1 corresponding to AU 2014200793 dated Sep. 2, 2017.

(Continued)

*Primary Examiner* — Nathaniel C Chukwurah
(74) *Attorney, Agent, or Firm* — Carter, DeLuca & Farrell LLP

(57) ABSTRACT

A loading unit includes a staple cartridge assembly, an anvil assembly, and an anvil hook assembly. The anvil assembly has an opening defined therethrough, and the anvil hook assembly includes an anvil hook disposed within the opening of the anvil assembly and a pivot pin extending through the anvil hook and the anvil assembly. The anvil hook is pivotable with respect to the anvil assembly about the pivot pin between a loading position and a loaded position. The loading unit may further include a surgical buttress assembly including a cartridge buttress releasably attached to the staple cartridge assembly, an anvil buttress releasably attachable to the anvil assembly by the anvil hook, and a connecting member interconnecting the cartridge and anvil buttresses.

20 Claims, 9 Drawing Sheets

(56) References Cited

U.S. PATENT DOCUMENTS

| | | |
|---|---|---|
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B2 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |

(56) References Cited

U.S. PATENT DOCUMENTS

| | | |
|---|---|---|
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |

(56) References Cited

U.S. PATENT DOCUMENTS

| | | |
|---|---|---|
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |

(56) References Cited

U.S. PATENT DOCUMENTS

| | | |
|---|---|---|
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0215132 A1* | 9/2011 | Aranyi .............. A61B 17/07207 227/176.1 |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1* | 8/2014 | Hodgkinson .... A61B 17/07292 227/180.1 |
| 2015/0041347 A1 | 2/2015 | Hodgkinson |
| 2015/0133995 A1 | 5/2015 | Shelton, IV et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.
Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.

(56) References Cited

OTHER PUBLICATIONS

European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.

(56) References Cited

OTHER PUBLICATIONS

Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).

(56) References Cited

OTHER PUBLICATIONS

Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

* cited by examiner

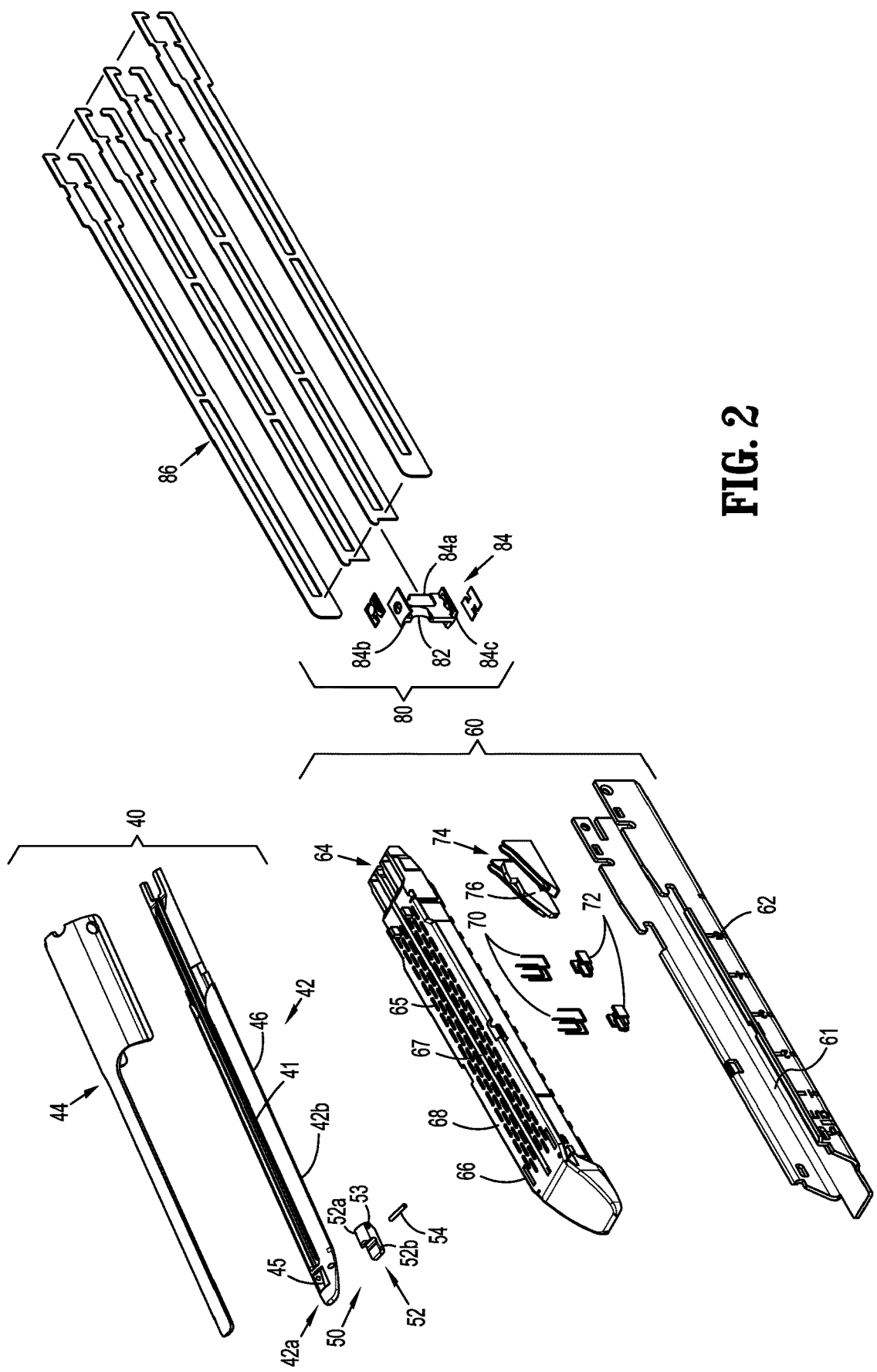

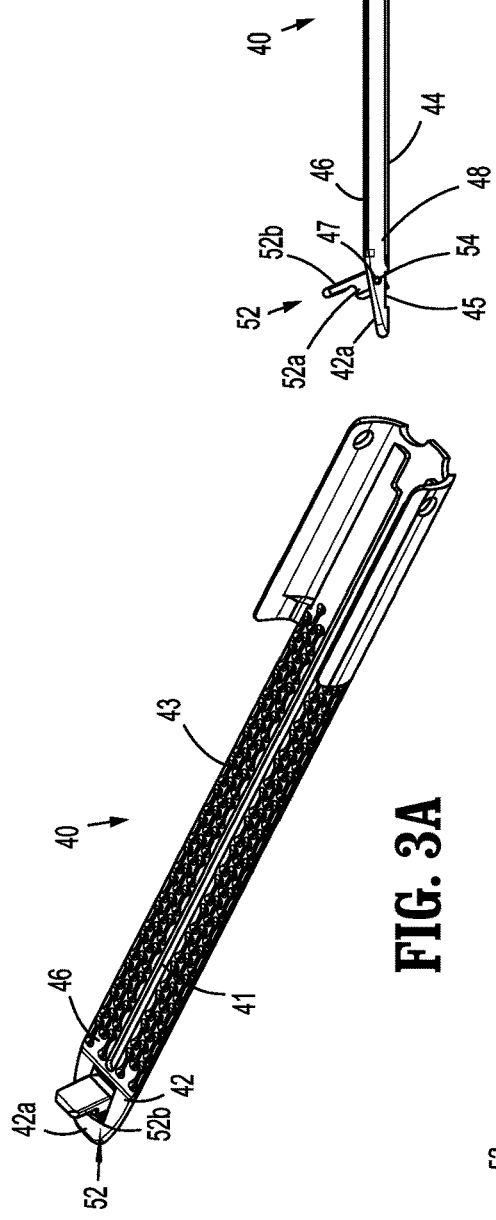
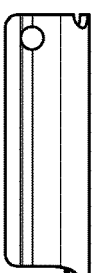
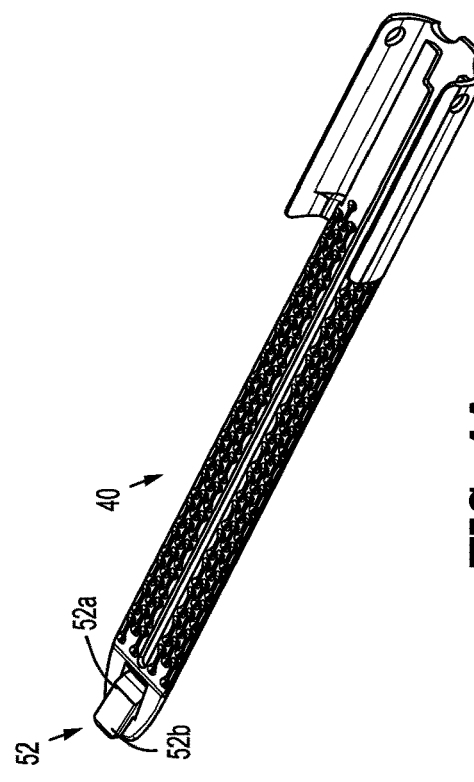
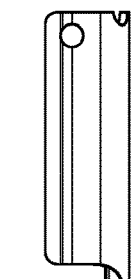

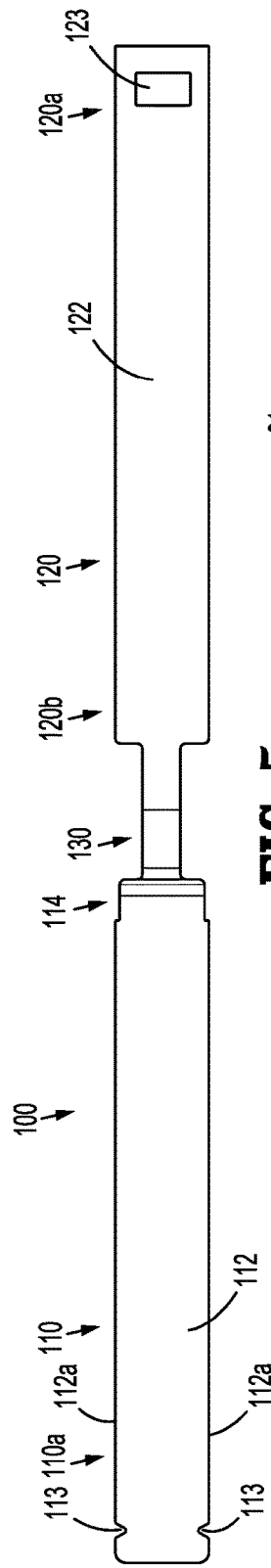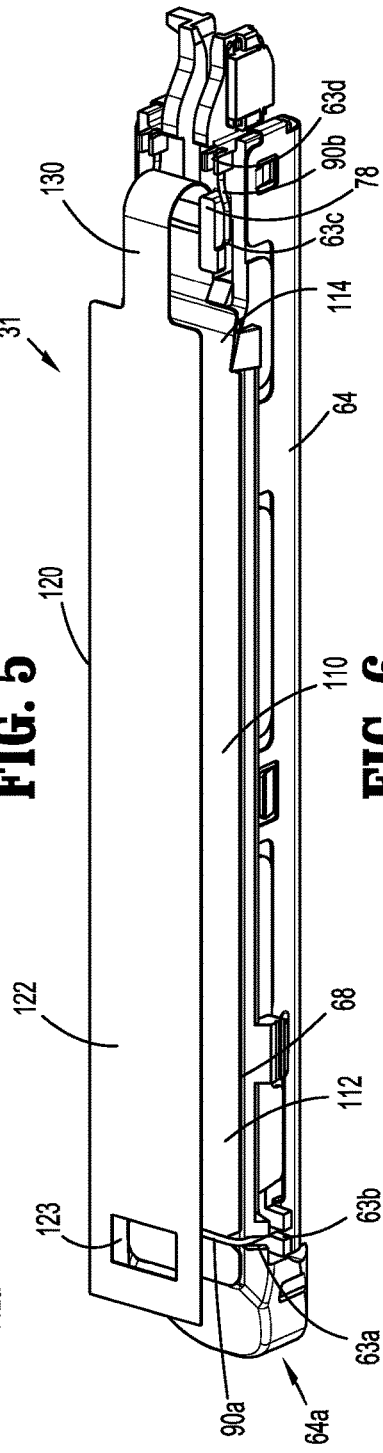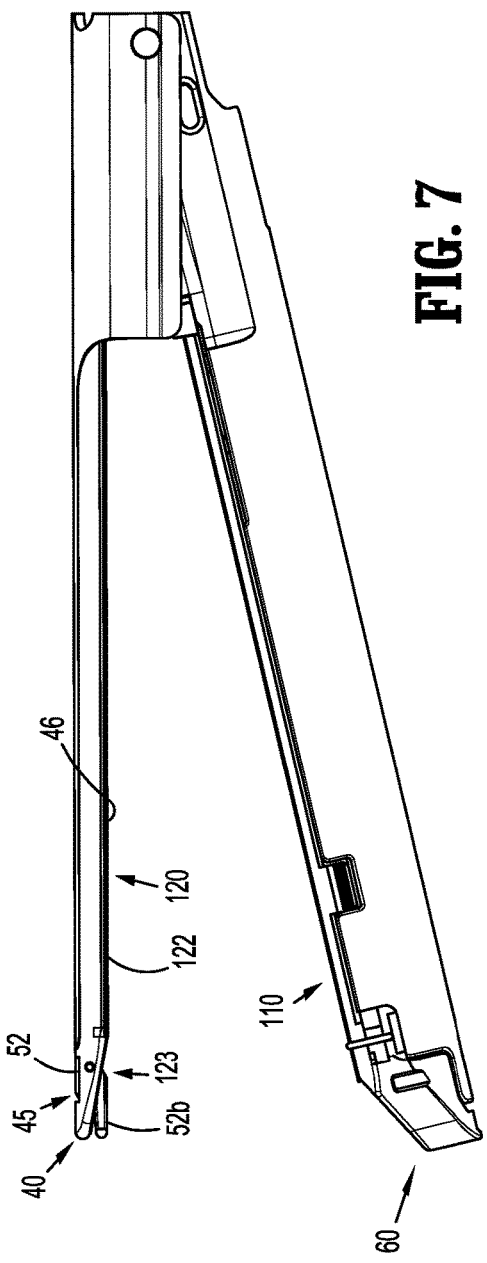

STAPLE LINE REINFORCEMENT FOR SURGICAL STAPLING APPARATUS

CROSS-REFERENCE TO RELATED APPLICATIONS

The present application claims the benefit of and priority to U.S. Provisional Patent Application Ser. No. 62/991,655, filed on Mar. 19, 2020, the entire content of which being hereby incorporated by reference.

FIELD

This application is generally related to surgical stapling apparatus, and more particularly, to loading units including anvil buttress attachment assemblies for releasably securing surgical buttresses to the surgical stapling apparatus.

BACKGROUND

Surgical stapling apparatus are employed by surgeons to sequentially or simultaneously apply one or more rows staples to body tissue for the purpose of joining segments of body tissue together. Such apparatus generally include a pair of jaws between which the body tissue to be joined is placed. When the surgical stapling apparatus is actuated, or "fired", firing bars contact staple drive members in one of the jaws. The staple drive members push the surgical staples through the body tissue and into an anvil in the opposite jaw which forms the staples. If body tissue is to be removed or separated, a knife blade can be provided in the jaws of the apparatus to cut the body tissue between the lines of staples.

Surgical supports, e.g., meshes or buttress materials, may be used in combination with surgical stapling apparatus to bridge, repair, and/or reinforce tissue defects within a patient. A clinician may manually attach the buttress materials to the surgical stapling apparatus in the operating room during a surgical procedure, or utilize a surgical stapling apparatus including buttress materials pre-installed thereon. The buttress material reinforces the staple or suture line as well as covers the juncture of the tissues to reduce leakage prior to healing.

SUMMARY

This disclosure generally relates to attachment of an anvil buttress material onto a loading unit of a surgical stapling apparatus having a pre-loaded cartridge buttress material. Anvil buttress attachment assemblies of the present disclosure are designed to make buttress material attachment in the operating room a simple, straightforward, and cost effective procedure.

In one aspect, the disclosure provides a loading unit including a staple cartridge assembly, an anvil assembly, and an anvil hook assembly. The anvil assembly has an opening defined therethrough, and the anvil hook assembly includes an anvil hook disposed within the opening of the anvil assembly and a pivot pin extending through the anvil hook and the anvil assembly. The anvil hook is pivotable with respect to the anvil assembly about the pivot pin between a loading position and a loaded position.

The opening of the anvil assembly may be defined in a distal portion of an anvil plate.

The anvil hook may include a body disposed within the opening of the anvil assembly and an arm extending from the body through a side of the opening open to a tissue facing surface of the anvil assembly. When the anvil hook is in the loading position, the arm may be disposed at a first angle with respect to the tissue facing surface of the anvil assembly and, when the anvil hook is in the loaded position, the arm may extend at a second angle with respect to the tissue facing surface of the anvil assembly.

The loading unit may further include a surgical buttress assembly including a cartridge buttress releasably attached to the staple cartridge assembly, an anvil buttress releasably attachable to the anvil assembly by the anvil hook, and a connecting member interconnecting the cartridge and anvil buttresses. The anvil buttress may include a cutout defined therethrough that is aligned with the opening of the anvil assembly such that the arm of the anvil hook extends through the cutout of the anvil buttress. Rotation of the anvil hook from the loading position to the loaded position may pull the anvil buttress distally and tension the anvil buttress against the anvil assembly.

The staple cartridge assembly may include a reload assembly including a staple cartridge. The cartridge buttress may be secured to the staple cartridge and the anvil buttress may overlie the cartridge buttress and be positionable against the anvil assembly. The connecting member of the surgical buttress assembly may be releasably secured to a tissue facing surface of the staple cartridge that is proximal of staple pockets defined in the tissue facing surface of the staple cartridge.

In another aspect, the disclosure provides for an anvil buttress attachment assembly including an anvil assembly and an anvil hook assembly. The anvil assembly has an opening defined therethrough, and the anvil hook assembly includes an anvil hook disposed within the opening of the anvil assembly and a pivot pin extending through the anvil hook and the anvil assembly. The anvil hook is pivotable with respect to the anvil assembly about the pivot pin between a loading position and a loaded position.

The opening of the anvil assembly may be defined in a distal portion of an anvil plate.

The anvil hook may include a body disposed within the opening of the anvil assembly and an arm extending from the body through a side of the opening open to a tissue facing surface of the anvil assembly. When the anvil hook is in the loading position, the arm may be disposed at a first angle with respect to the tissue facing surface of the anvil assembly and, when the anvil hook is in the loaded position, the arm may extend at a second angle with respect to the tissue facing surface of the anvil assembly.

The anvil buttress attachment assembly may further include an anvil buttress releasably attachable to the anvil assembly by the anvil hook. The anvil buttress may include a cutout defined therethrough that is aligned with the opening of the anvil assembly such that the arm of the anvil hook extends through the cutout of the anvil buttress. Rotation of the anvil hook from the loading position to the loaded position may pull the anvil buttress distally and tension the anvil buttress against the anvil assembly. The anvil buttress attachment assembly may further include a cartridge buttress coupled to the anvil buttress by a connecting member.

In yet another aspect, the disclosure provides an anvil buttress attachment assembly including an anvil assembly and an anvil hook. The anvil assembly has an opening defined therethrough, and the anvil hook is removably positionable within the opening defined in the anvil assembly. The anvil hook includes a body having an arm on a proximal end of the body that is biased in a proximal position to snap into a cavity of the anvil assembly when the anvil hook is loaded into the opening. The arm is deflectable in a distal direction to remove the anvil hook from the opening of the anvil assembly.

The opening of the anvil assembly may be defined in a distal portion of an anvil plate.

The anvil hook may include a lip extending distally from the body. When the body of the anvil hook is loaded into the opening of the anvil assembly, the lip may be positioned over a distal portion of the anvil assembly.

The anvil buttress attachment assembly may further include an anvil buttress releasably attachable to the anvil assembly by the anvil hook. The anvil buttress may include a cutout defined therethrough that is aligned with the opening defined in the anvil assembly. The lip of the anvil hook may hold the anvil buttress against the anvil assembly when the anvil hook is loaded into the opening of the anvil assembly.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

FIG. 2 is an exploded, perspective view of a tool assembly of the surgical stapling apparatus of FIG. 1 in accordance with an aspect of the disclosure;

FIG. 3A is a bottom, perspective view of an anvil assembly of the tool assembly of FIG. 2, shown with an anvil hook in a loading position;

FIG. 3B is a side view of the anvil assembly of FIG. 3A;

FIG. 4A is a bottom, perspective view of an anvil assembly of the tool assembly of FIG. 2, shown with an anvil hook in a loaded position;

FIG. 4B is a side view of the anvil assembly of FIG. 4A;

FIG. 5 is a plan view of a surgical buttress assembly for use with the surgical stapling apparatus of FIG. 1;

FIG. 6 is a top, perspective view of a reload assembly including the surgical buttress assembly of FIG. 5 for use with a loading unit of the surgical stapling apparatus of FIG. 1 in accordance with an aspect of the disclosure;

FIG. 7 is a side view of the reload assembly of FIG. 6 disposed within the loading unit of the surgical stapling apparatus of FIG. 1, shown with the surgical buttress assembly attached to anvil and staple cartridge assemblies of the loading unit;

DETAILED DESCRIPTION

Figure 1:
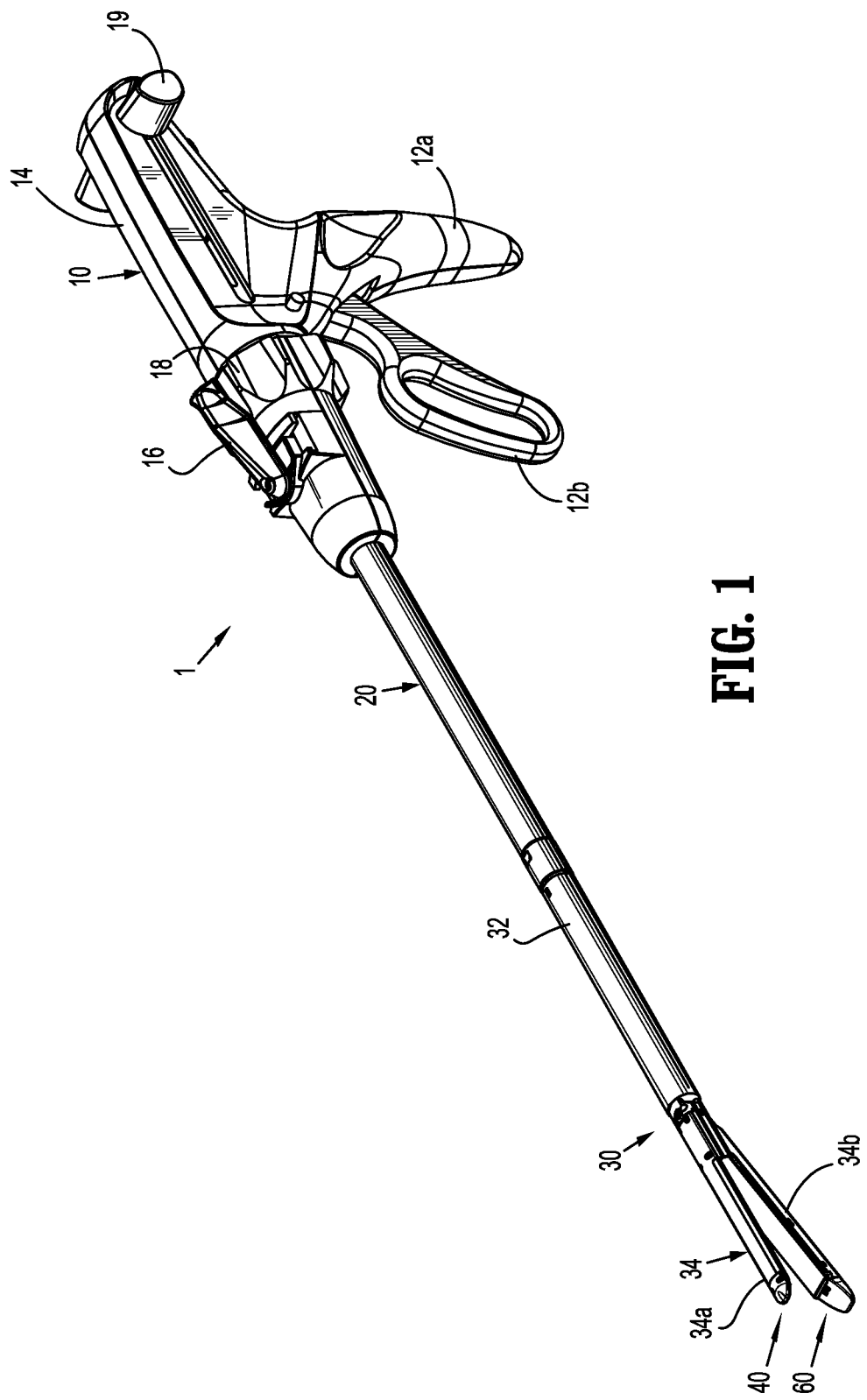
FIG. 1 is a perspective view of a surgical stapling apparatus in accordance with an embodiment of the disclosure.

Aspects of this disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user.

Referring now to FIG. 1, an exemplary surgical stapling apparatus or surgical stapler 1 is shown for use in stapling tissue in accordance with an aspect of this disclosure. The surgical stapling apparatus 1 generally includes a handle assembly 10, an elongate tubular body 20 extending distally from the handle assembly 10, and a loading unit 30 extending distally from the elongate tubular body 20. The loading unit 30 includes a housing portion 32 and a tool or jaw assembly 34 including first and second jaw members 34a, 34b. The first jaw member 34a and/or the second jaw members 34b is pivotable with respect to the housing portion 32 such that the tool assembly 34 is movable between an open position in which the first and second jaw members 34a, 34b are spaced apart with respect to each other, and a closed position in which the first and second jaw members 34a, 34b are substantially adjacent each other.

The handle assembly 10 includes a stationary handle member 12a, a movable handle member 12b, and a barrel portion 14. Actuation of the movable handle member 12b applies lines of staples 70 (FIG. 2) to tissue captured between the first and second jaw members 34a, 34b of the tool assembly 34. An articulation lever 16 is mounted on the forward end of the barrel portion 14 to facilitate articulation of the tool assembly 34. A rotatable member 18 is also mounted on the forward end of the barrel portion 14, adjacent the articulation lever 16. Rotation of the rotatable member 18 relative to the barrel portion 14 rotates the elongate tubular body 20 and the loading unit 30 relative to the handle assembly 10 so as to properly orient the tool assembly 34 relative to tissue to be stapled. A pair of knobs 19 is movably positionable along the barrel portion 14. The pair of knobs 19 is advanced distally to approximate or close the first and second jaw members 34a, 34b of the tool assembly 34 relative to each other, and retracted proximally to unapproximate or open the first and second jaw members 34a, 34b of the tool assembly 34 with respect to each other.

The loading unit 30 is a disposable loading unit ("DLU") that is releasably secured to the elongated tubular body 20 and thus, replaceable with a new loading unit 30. The loading unit 30 may be a single use loading unit ("SULU") that is used one time and then replaced to facilitate multiples uses of the surgical stapling apparatus 1 on a patient. For example, during a surgical procedure, the surgical stapling apparatus 1 can be used to staple and cut tissue, and the entire SULU is replaced after each staple and cut operation of the surgical stapling apparatus 1. The loading unit 30 may be a multi-use loading unit ("MULU") that is re-useable a predetermined number of times. For example, during a surgical procedure, the surgical stapling apparatus 1 can be used to staple and cut tissue, and a reload assembly 31 (see e.g., FIG. 6) of the MULU is replaced after each staple and cut operation of the surgical stapling apparatus 1 a predetermined number of times before the entire MULU needs to be replaced. Alternatively, the loading unit 30 may be permanently affixed to the elongated tubular body 20.

As shown in FIGS. 1 and 2, the first jaw member 34a of the tool assembly 34 includes an anvil assembly 40 and the second jaw member 34b of the tool assembly 34 includes a staple cartridge assembly 60. The anvil assembly 40 includes an anvil plate 42 and a cover plate 44 secured over the anvil plate 42. The anvil plate 42 has a central longitudinal slot 41 formed therein and a plurality of staple forming pockets or cavities 43 (FIG. 3A) defined in an inward or tissue facing surface thereof 46. As seen in FIGS. 3A and 3B, in conjunction with FIG. 2, the tissue facing surface 46 is substantially planar along the length having the staple forming pockets 43 defined therein, with a distal portion 42a of the anvil plate 42, which extends distal to the staple forming pockets 43, being angled outwardly or tapering towards an outer surface 48 of the anvil assembly 40. The distal portion 42a of the anvil plate 42 also extends distally beyond the cover plate 44 and incudes an opening 45 defined therethrough which is operably coupled to an anvil hook assembly 50. The anvil hook assembly 50 includes an anvil swing hook 52 (also referred to herein as an anvil hook) and a pivot pin 54 pivotably coupling the anvil hook 52 to the anvil plate 42.

As shown in FIGS. 2-4B, the anvil hook 52 includes a body 52a positioned within the opening 45 of the anvil plate 42, and an arm 52b extending from the body 52a out through the opening 45 on the side of the anvil plate 42 including the tissue facing surface 46. The body 52a of the anvil hook 52 includes an aperture 53 extending transversely therethrough that is aligned with apertures 47 defined in longitudinal sides 42b of the anvil plate 42 for reception of the pivot pin 54 therethrough. The pivot pin 54 extends through the apertures 47 of the anvil plate 42 and through the aperture 53 of the anvil hook 52 to pivotably couple the anvil hook 52 to the anvil plate 42.

The anvil hook 52 is pivotable about the pivot pin 54 between an open or loading position, seen in FIGS. 3A and 3B, and a closed or loaded position, seen in FIGS. 4A and 4B. In the open position, the arm 52b of the anvil hook 52 extends outwardly in an upward direction through the opening 45 of the anvil plate 42 forming a first angle (e.g., a right or acute angle) with respect to the distal portion 42a of the anvil plate 42. In the closed position, the arm 52b of the anvil hook 52 extends outwardly in a distal direction forming a second angle with respect to the distal portion 42a of the anvil plate 42, which is smaller than the first angle, and is substantially aligned with the tissue facing surface 46 of the anvil plate 42.

With reference again to FIG. 2, the staple cartridge assembly 60 includes a cartridge carrier 62 defining an elongated support channel 61 configured and dimensioned to selectively receive and support a staple cartridge 64 therein. The staple cartridge 64 may be removably and/or replaceably attached to the cartridge carrier 62 by, for example, a snap-fit connection, a detent, a latch, among other types of connectors within the purview of those skilled in the art. The staple cartridge 64 includes a cartridge body 66 having an inward or tissue facing surface 68 defining staple pockets or retention slots 65 formed therein for receiving a plurality of fasteners or staples 70 and staple pushers 72. A central longitudinal slot 67 is formed in and extends along a substantial length of the cartridge body 66 to facilitate passage of a knife blade 82 of a drive assembly 80 therethrough.

The knife blade 82 is defined in a distal edge of a central wall portion 84a of an I-beam 84 that is operatively associated with the tool assembly 34. The central wall portion 84a of the I-beam 84 is slidably disposed between the anvil and staple cartridge assemblies 40, 60, with upper and lower rails 84b, 84c of the I-beam 84, respectively, supported in the anvil and staple cartridge assemblies 40, 60. The I-beam 84 is coupled to an elongated drive beam 86 which is configured to engage a drive member (not shown) of the elongated tubular body 20 (FIG. 1) of the surgical stapling apparatus 1 when the loading unit 30 is engaged therewith. The drive member imparts axial movement to the elongated drive beam 86 and thus, the I-beam 84, from the handle assembly 10. Accordingly, during operation of the surgical stapling apparatus 1, distal advancement of the I-beam 84 causes an actuation sled 74 to translate through the staple cartridge 64 and to advance cam wedges 76 of the actuation sled 74 into sequential contact with the staple pushers 72 which, in turn, cause the staple pushers 72 to translate vertically within the staple pockets 65 and urge the staples 70 from the staple pockets 65 towards the tissue facing surface 46 of the anvil plate 42 of the anvil assembly 40.

For a detailed description of the structure and function of exemplary surgical stapling apparatus, reference may be made to U.S. Pat. Nos. 6,241,139, 6,330,965, and 7,819,896, the entire contents of each of which are incorporated herein by reference. It should be appreciated that principles of this disclosure are equally applicable to surgical stapling apparatus having other configurations such as, for example, the types described in U.S. Pat. Nos. 5,964,394, 7,128,253, and 7,334,717, the entire contents of each of which are incorporated herein by reference. Accordingly, it should be understood that a variety of surgical stapling apparatus may be utilized with the techniques of this disclosure. For example, laparoscopic or open staplers, such as, for example, GIA™, Endo GIA™, TA™, and Endo TA™ staplers and/or linear and radial reloads with, for example, Tri-Staple™ technology, available through Medtronic (North Haven, Conn.) may be utilized with the anvil buttress attachment assemblies of this disclosure.

With reference now to FIG. 5, a surgical buttress assembly 100 for use with the loading unit 30 (FIG. 1) is shown. The surgical buttress assembly 100 includes a cartridge buttress 110 and an anvil buttress 120 interconnected by a connecting member 130. The cartridge buttress 110 includes a body portion 112 having a pair of distal recesses 113 defined in opposing longitudinal edges 112a of the body portion 112 about a distal end portion 110a of the cartridge buttress 110, and a tail portion 114 extending proximally from the body portion 112. The tail portion 114 has a smaller dimension (e.g., a smaller width and/or length) than the body portion 112. The anvil buttress 120 includes a body portion 122 having an opening or cutout 123 defined in the body portion 122 about a distal end portion 120a of the anvil buttress 120. The connecting member 130 extends from the tail portion 114 of the cartridge buttress 110 and a proximal end portion 120b of the anvil buttress 120. The connecting member 130 has a smaller dimension (e.g., a smaller width and/or length) than the cartridge and anvil buttresses 110, 120.

The cartridge and anvil buttresses 110, 120 (also referred to herein generally as surgical buttresses or buttress materials) are fabricated from biocompatible materials which are bioabsorbable or non-absorbable, natural or synthetic materials. It should be understood that any combination of natural, synthetic, bioabsorbable, and/or non-bioabsorbable materials may be used to form the cartridge and anvil buttresses 110, 120. The cartridge and anvil buttresses 110, 120 may be formed from the same material or different materials.

The cartridge and anvil buttresses 110, 120 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The cartridge and anvil buttresses 110, 120 described herein may be a single porous or non-porous layer, or include a plurality of layers including any combination of porous and non-porous layers. For example, the cartridge and/or anvil buttress may include multiple porous and non-porous layers that are stacked in an alternating manner. In another example, the cartridge and/or anvil buttress may be formed in a "sandwich-like" manner wherein the outer layers of the surgical buttress are porous and the inner layer(s) are non-porous, or vice versa. The cartridge and anvil buttresses 110, 120 may have the same or a different structure of layer(s).

Porous layer(s) in a surgical buttress may enhance the ability of the surgical buttress to absorb fluid, reduce bleeding, and/or seal a wound. Also, the porous layer(s) may allow for tissue ingrowth to fix the surgical buttress in place. Non-porous layer(s) in a surgical buttress may enhance the ability of the surgical buttress to resist tears and perforations during the manufacturing, shipping, handling, and/or stapling processes. Also, non-porous layer(s) may retard or prevent tissue ingrowth from surrounding tissues thereby acting as an adhesion barrier and preventing the formation of unwanted scar tissue.

The connecting member 130 is also fabricated from biocompatible materials, and may be formed from the same or different materials as the cartridge buttress 110 and/or the anvil buttress 120. In certain aspects, the surgical buttress assembly 100 is formed from a single sheet of material that is cut to shape. In other aspects, the connecting member 130 may be a suture, cord, strap, etc. secured to the cartridge and anvil buttresses 110, 120.

With reference to FIGS. 5 and 6, the body portion 112 of the cartridge buttress 110 is configured and dimensioned to overlie the tissue facing surface 68 of the staple cartridge 64 with the pair of distal recesses 113 aligned with a first pair of distal slots 63a formed in opposed sides of a distal portion 64a of the staple cartridge 64. The pair of distal recesses 113 of the cartridge buttress 110 and the first pair of distal slots 63a of the staple cartridge 64 are utilized together with a second pair of distal slots 63b to secure the distal end portion 110a of the cartridge buttress 110 to the distal portion 64a of the staple cartridge 64 via a first retention member 90a.

The tail portion 114 of the cartridge buttress 110 overlies the tissue facing surface 68 of the staple cartridge 64 proximal of the staple pockets 65 (FIG. 2) defined in the tissue facing surface 68. The connecting member 130 extends proximally from the tail portion 114 and is releasably secured between a pair of raised rails 78 of the staple cartridge 64 by a second retention member 90b. The staple cartridge 64 includes a first pair of proximal slots 63c formed in the raised rails 78 and a second pair of proximal slots 63d disposed proximal to the first pair of proximal slots 63c. The second retention member 90b is threaded through the first pair of proximal slots 63c such that the second retention member 90b extends across the connecting member 130 and then is positioned through the second pair of proximal slots 63d to secure the connecting member 130 and thus, the tail portion 114 of the cartridge buttress 110 to the staple cartridge 64. The connecting member 130 is then looped over itself such that the anvil buttress 120 overlies the cartridge buttress 110.

The first and/or second pairs of distal and/or proximal slots 63a-63d may have a circular or non-circular configuration dimensioned to retain portions of the respective first and second retention members 90a, 90b therein (e.g., frictionally engaging, pinching, or otherwise constricting the first and second retention members 90a, 90b) to maintain placement of the first and second retention members 90a, 90b across the distal portion 110a of the cartridge buttress 110 and the connecting member 130, respectively. The first pair of distal and proximal slots 63a, 63c is configured such that the first and second retention members 90a, 90b extend across a path of the knife blade 82 (FIG. 2).

The first and second retention members 90a, 90b are fabricated from biocompatible materials which are any combination of natural, synthetic, bioabsorbable, and/or non-bioabsorbable materials. Each of the first and second retention members 90a, 90b is a single continuous elongated structure, and may be in the form of a suture, thread, filament, tether, strap, band, line, wire, cable, etc. Alternatively, the first and second retention members 90a, 90b may be secured to the staple cartridge 64 via other attachment features or methods, such as chemical attachment features (e.g., adhesives), mechanical attachment features (e.g., mounting structures such as tabs or pins), and/or attachment methods (e.g., welding), to releasably secure the cartridge buttress 110 and/or the connecting member 130 to the staple cartridge 64.

As shown in FIGS. 5-7, the body portion 122 of the anvil buttress 120 is configured and dimensioned to overlie the tissue facing surface 46 of the anvil assembly 40, with the cutout 123 of the anvil buttress 120 aligned with the opening 45 defined in the anvil assembly 40 and the arm 52b of the anvil hook 52 extending through the cutout 123 in the closed position to secure the anvil buttress 120 to the anvil assembly 40. As the connecting member 130 is releasably secured to the staple cartridge 64 and looped towards the anvil assembly 40, the tool assembly 34 (FIG. 1) may open, close, and otherwise function (e.g., grasp and/or staple tissue) without putting stress on the second retention member 90b (e.g., the portion of the connecting member 130 disposed proximal of the second retention member 90 provides slack to the surgical buttress assembly 100 during movement of the anvil and/or staple cartridge assemblies 40, 60), and the attachment of the distal end portions 110a, 120a of the cartridge and anvil buttresses 110, 120 do not interfere with the function of the tool assembly 34 when the surgical buttress assembly 100 is loaded onto the loading unit 30.

Figure 8:
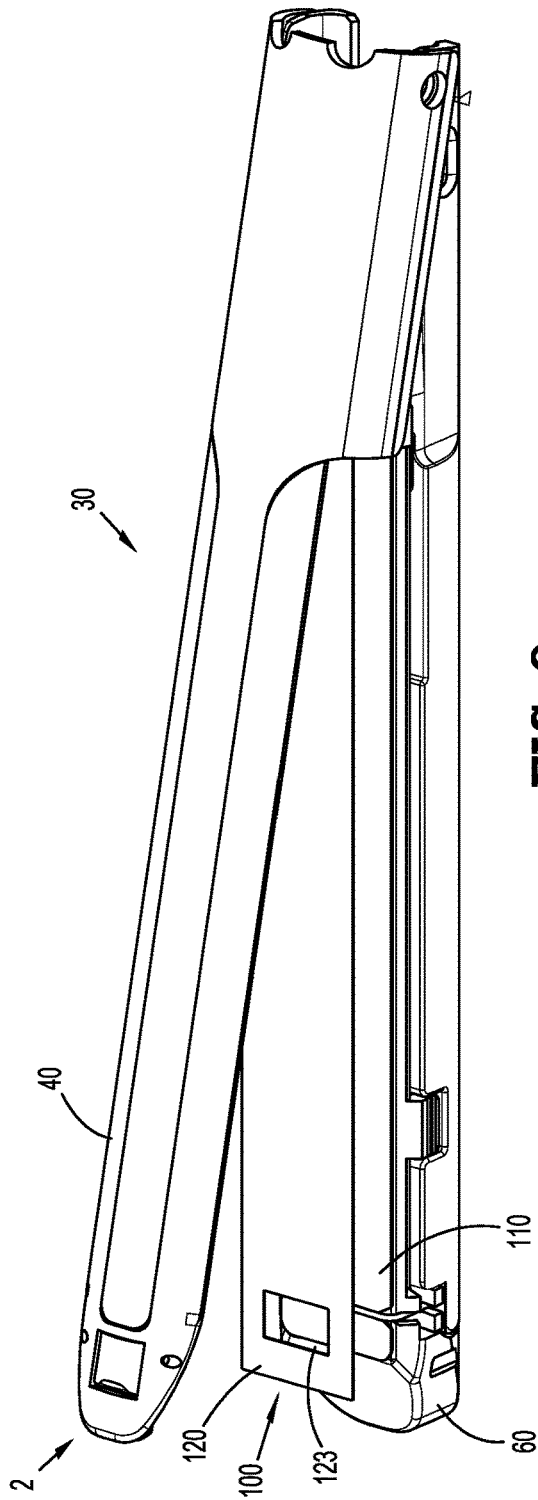
FIG. 8 is a perspective view of the reload assembly of FIG. 6 disposed within the loading unit of the surgical stapling apparatus of FIG. 1 prior to attaching an anvil buttress of the surgical buttress assembly onto an anvil assembly of the loading unit via an anvil buttress attachment assembly in accordance with an aspect of the disclosure.

FIG. 8 illustrates a loading unit 30 including the cartridge buttress 110 of the surgical buttress assembly 100 secured to the staple cartridge assembly 60, and the anvil buttress 120 freely disposed between the anvil and cartridge assemblies 40, 60. In aspects, the surgical buttress assembly 100 is pre-loaded (e.g., by the manufacturer) onto a reload assembly 31 (FIG. 6) with the cartridge buttress 110 secured to the staple cartridge 64 and the anvil buttress 120 free from attachment, and the reload assembly 31 is positioned within the loading unit 30. The loading unit 30 includes an anvil buttress retention assembly 2 for loading of the anvil buttress 120 onto the anvil assembly 40.

In a method of loading the anvil buttress 120 of the surgical buttress assembly 100 onto the anvil assembly 40 of the loading unit 30, in which the cartridge buttress 110 is already secured to the staple cartridge assembly 60, the body portion 122 of the anvil buttress 120 is positioned adjacent to the tissue facing surface 46 of the anvil assembly 40 with the anvil hook 52 of the anvil hook assembly 50 disposed in the open position, as shown in FIGS. 9A-9E. With the anvil hook 52 in the open position, the cutout 123 in the anvil buttress 120 is aligned with the opening 45 of the anvil plate 40, and the arm 52b of the anvil hook 52 extends through the cutout 123 of the anvil buttress 120. The anvil buttress 120 is substantially planar such that the body portion 122 of the anvil buttress 120 is positioned directly against the tissue facing surface 46 and the distal end portion 120a of the anvil buttress 120 is spaced from the distal portion 42a of the anvil plate 42.

Figure 9B:
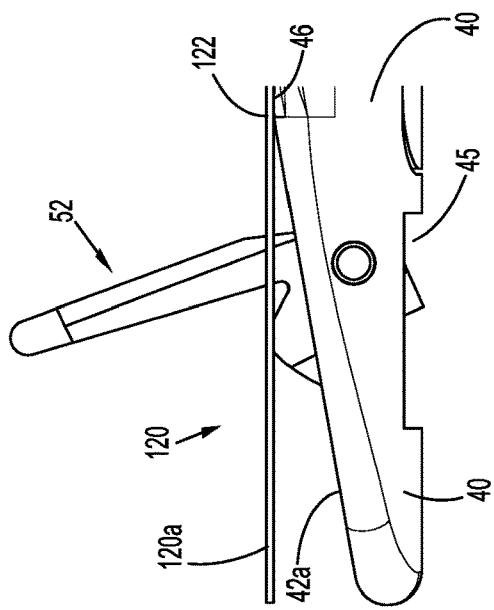
FIG. 9B is a close-up view of a distal portion of the anvil assembly of FIG. 9A.
Figure 9A:
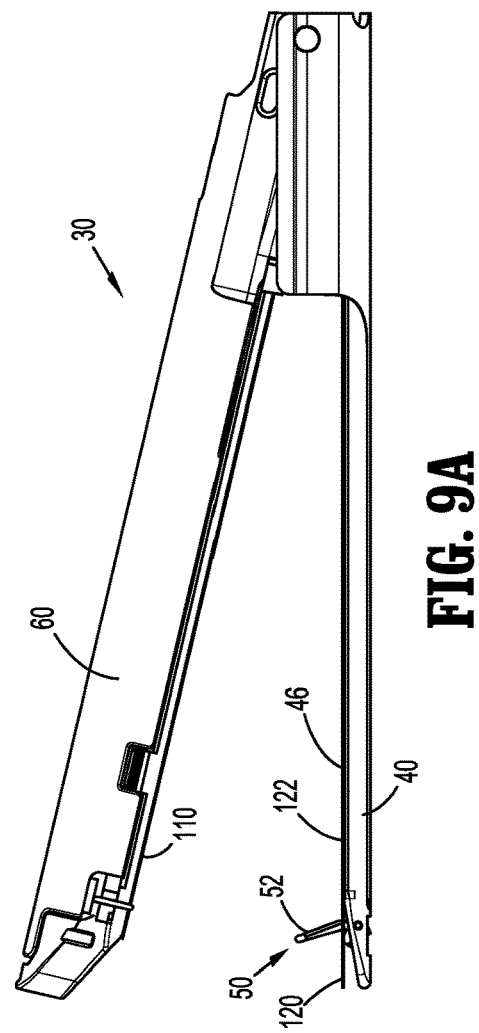
FIG. 9A is a side view of the loading unit of FIG. 8, shown with the anvil buttress position against the anvil assembly and an anvil hook disposed in the loading position.
Figure 9C:
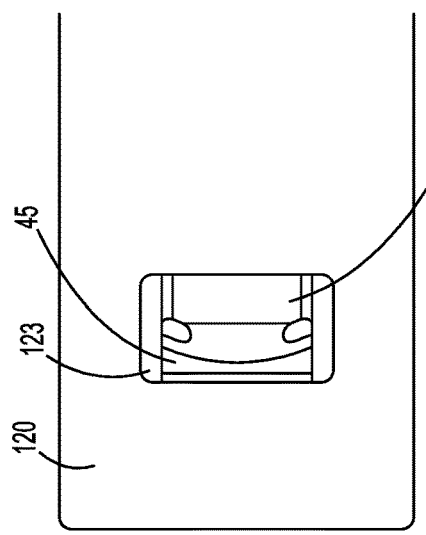
FIG. 9C is a side, cross-sectional view of the loading unit of FIG. 9A.
Figure 9D:
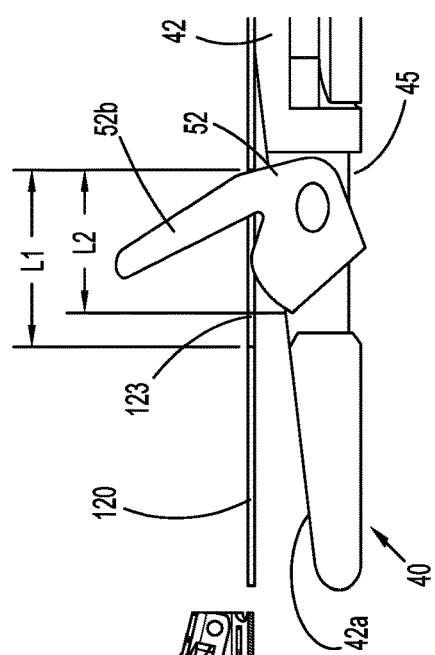
FIG. 9D is a close-up view of a distal portion of the anvil assembly of FIG. 9C.
Figure 9E:
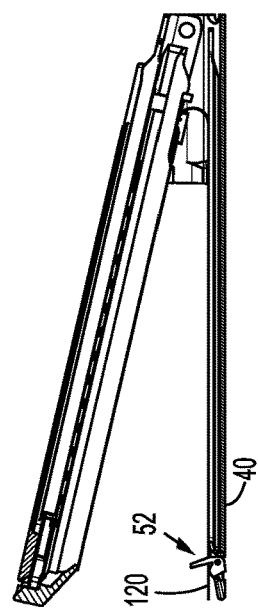
FIG. 9E is a top view of the anvil buttress and the anvil assembly of FIG. 9D.
Figure 10B:
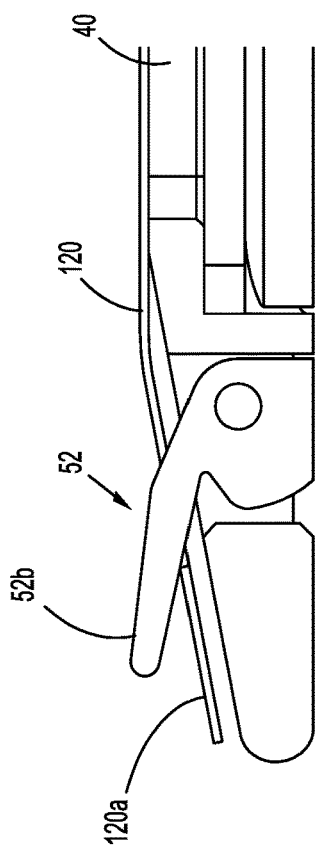
FIG. 10B is a close-up view of a distal portion of the anvil assembly of FIG. 9C, shown with the anvil hook disposed in the loaded position and retaining the anvil buttress against the anvil assembly.
Figure 10A:
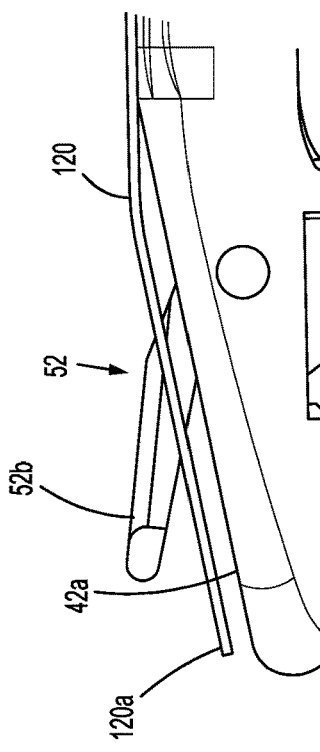
FIG. 10A is a close-up view of a distal portion of the anvil assembly of FIG. 9A, shown with the anvil hook disposed in the loaded position and retaining the anvil buttress against the anvil assembly.

As seen in FIGS. 9D and 9E, in the open position, the cutout 123 of the anvil buttress 120 is aligned with the anvil hook 52 such that the size (e.g., the length "L1") of the cutout 123 is substantially the same as or just bigger than the size (e.g., the length "L2") of the anvil hook 52 when the anvil hook 52 is disposed in the open position. Accordingly, once the anvil buttress 120 is positioned against the anvil plate 42, as described above, the arm 52b of the anvil hook 52 is rotated (e.g., pushed in a distal direction towards the distal portion 42a of the anvil assembly 40) such that the arm 52b of the anvil hook 52 engages the anvil buttress 120 (e.g., by interference fit) causing the anvil buttress 120 to move distally until the anvil hook 52 is in the closed position as shown in FIGS. 10A and 10B. In the closed position, the anvil buttress 120 is held under tension by the arm 52b of the anvil hook 52 against the anvil assembly 40, and the anvil hook 52 pulls the distal end portion 120a of the anvil buttress 120 against the distal portion 42a of the anvil plate 42. This tension holds the anvil buttress 120 firmly against the tissue facing surface 46 of the anvil assembly 40 during tissue manipulation and firing of the surgical stapling apparatus 1.

In operation, with the loading unit 30 loaded with both the cartridge and anvil buttresses 110, 120 of the surgical buttress assembly 100, as described above, the surgical stapling apparatus 1 is used in accordance with methods known by those skilled in the art. Once the anvil and staple cartridge assemblies 40, 60 are clamped onto tissue, the surgical stapling apparatus 1 is fired, thereby stapling the cartridge and anvil buttresses 110, 120 to the tissue.

During firing, the knife blade 68 of the I-beam 70 travels distally through the tool assembly 34 and substantially simultaneously cuts and divides the tissue and the surgical buttresses 110, 120 disposed between the rows of formed staples 70. As the first and second retention members 90a, 90b extend across the respective distal end portion 110a and tail portion 114 of the cartridge buttress 110, above the central longitudinal slot 67 of the staple cartridge assembly 60, the knife blade 68 also cuts through the second retention member 90b and then the first retention member 90a thereby freeing the cartridge buttress 110 from the staple cartridge assembly 60. The knife blade 68 also cuts through the anvil buttress 110 into the cutout 123 such that when firing is complete and the anvil and staple cartridge assemblies 40, 60 are unclamped, the cartridge and anvil buttresses 110, 120, which are now stapled to the tissue, pull away from the staple cartridge and anvil assemblies 60, 40, and the tool assembly 34 can be removed from the surgical site. The used reload assembly 31 may then be removed from the tool assembly 34 by removing the staple cartridge 64 from the staple cartridge assembly 60, and the anvil hook 52 may be returned to the open position by pushing the arm 52b of the anvil hook 52 proximally towards the staple cartridge assembly 60. In aspects, additional or replacement reload assemblies 31 including the pre-loaded cartridge buttress 110 may be secured to the loading unit 30, as needed or desired, and the anvil buttress 120 may be secured to the loading unit 30, as described above.

Figure 11:
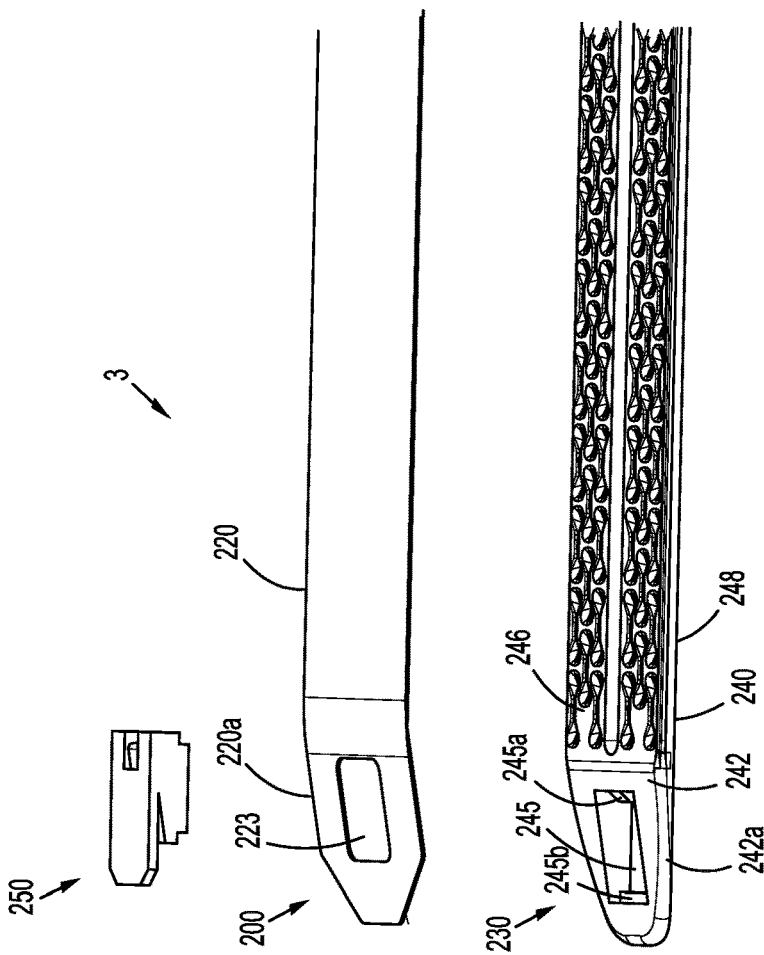
FIG. 11 is a perspective view, with parts separated, of an anvil buttress attachment assembly in accordance with another aspect of the disclosure.

With reference now to FIG. 11, an anvil buttress retention system 3 in accordance with another aspect of this disclosure is shown. The anvil buttress retention system 3 includes a loading unit 230 including an anvil assembly 240, an anvil snap hook 250 (also referred to herein as an anvil hook), and a surgical buttress assembly 200. The anvil assembly 240 is substantially the same as the anvil assembly 140, except that the distal portion 242a of the anvil plate 242 defines an opening 245 therethrough that is configured to removable receive the anvil hook 250 therein. The opening 245 is stepped at the proximal and distal ends 245a, 245b thereof, with the portion of the opening 245 open to the tissue facing surface 246 of the anvil assembly 240 being larger than the portion of the opening 245 open to the outer surface 248 of the anvil assembly 240.

The surgical buttress assembly 200 is substantially the same as the surgical buttress assembly 100 described above, and includes a cartridge buttress 110 and a connecting member 120 (FIG. 5), and an anvil buttress 220. The anvil buttress 220 includes a distal end portion 220a that is sized and shaped mimic the size and shape of the distal end 242a of the anvil assembly 240, and defines a cutout 223 therein that corresponds to the size and shape of the opening 245 defined through the anvil assembly 240 (e.g., corresponding to the size and shape of the portion of the opening 245 open to the tissue facing surface 246 of the anvil assembly 240).

Figure 12A:
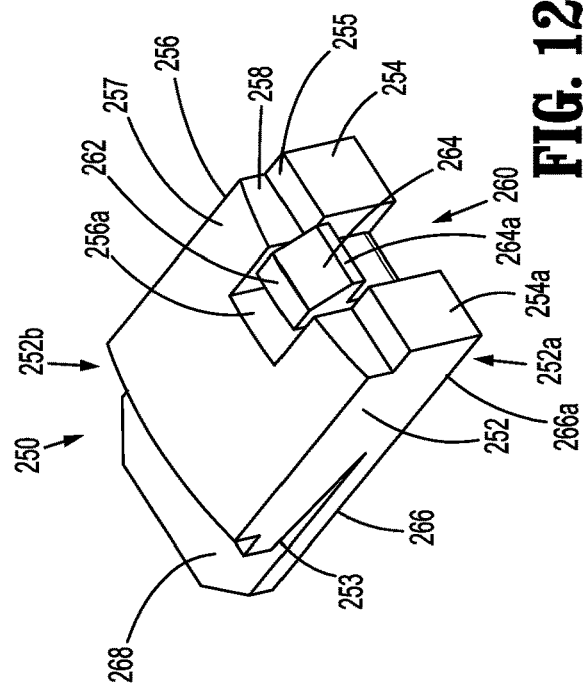
FIGS. 12A and 12B are perspective views of an anvil hook of the anvil buttress attachment assembly of FIG. 11.
Figure 12B:
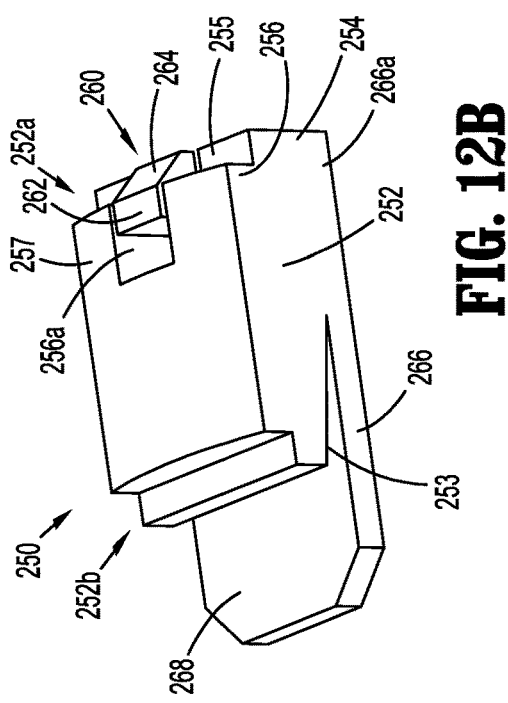

As shown in FIGS. 11-12B, the anvil hook 250 includes a body 252 sized and shaped to be received within the opening 245 of the anvil assembly 240. The body 252 has a tiered structure including a base tier 254 having a base surface 255 and a raised tier 256 having a raised surface 257, the base and raised surfaces 255, 257 stepped relative to each other on proximal and distal end portions 252a, 252b of the body 252 such that the base surface 255 extends proximally and distally beyond the raised surface 257. An intermediate wall 258 interconnects the base and raised surfaces 255, 257 at the proximal and distal end portions 252a, 252b of the body 252.

The raised tier 256 includes an arm 260 on the proximal end portion 252a of the body 252. The arm 260 includes a wall segment 262 disposed within a cavity 256a of the raised tier 256, and a protruding segment 264 extending proximally from the wall segment 262. A proximal end 264a of the protruding segment 264 is aligned with a proximal end 254a of the base tier 254. The arm 260 is biased in a proximal position, as see in FIGS. 12A and 12B, and is movable in a distal direction into the cavity 256a of the raised tier 256.

The anvil hook 250 includes a platform 266 coupled to (e.g., integrally formed with) the body 252. The platform 266 extends from the base tier 254 of the body 252 on a side opposed from the raised tier 256. The platform 266 includes a proximal portion 266a that is coterminous with the base tier 254 and a lip 268 that extends distally beyond the base tier 254. The base tier 254 includes a tapered wall 253 opposed from the platform 266 that defines an angled space between the base tier 254 and the platform 266.

Figure 13:
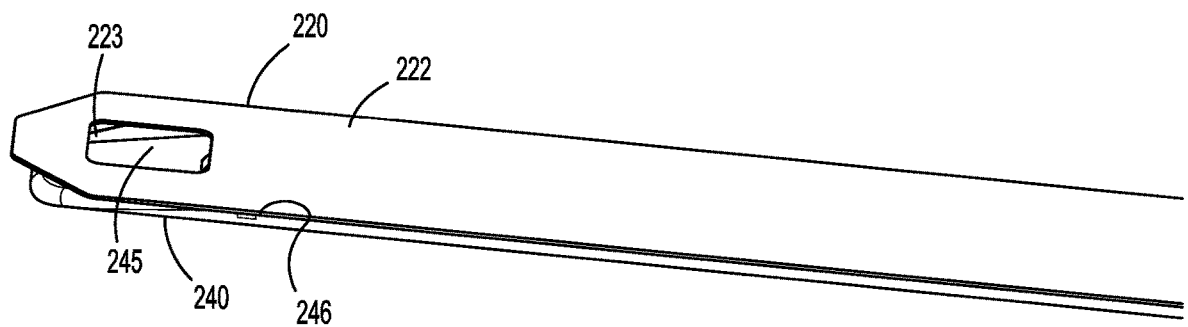
FIG. 13 is a top view of an anvil buttress positioned over an anvil assembly of the anvil buttress attachment assembly of FIG. 11.
Figure 14:
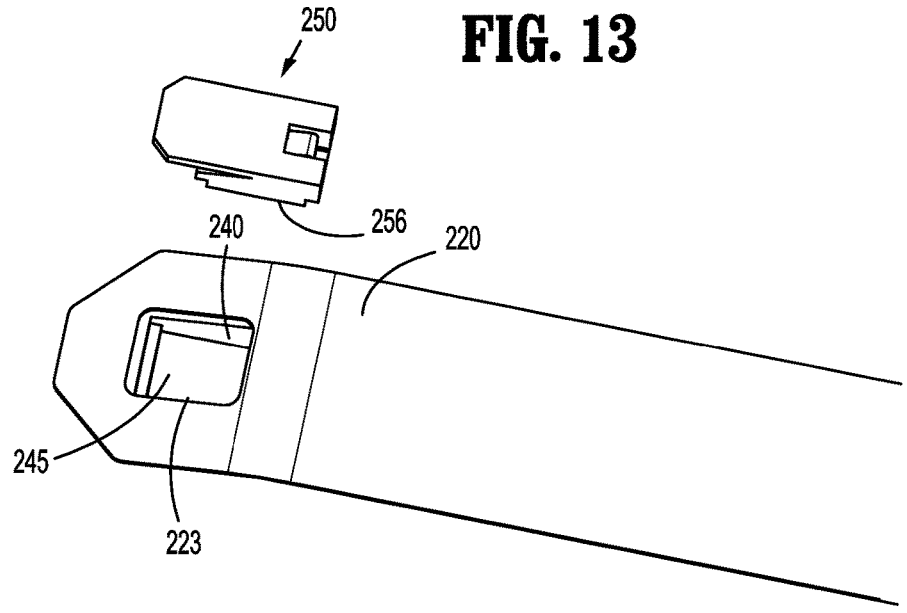
FIG. 14 is a top view of an anvil hook of the anvil buttress attachment assembly of FIG. 11 being positioned through the anvil buttress and the anvil assembly of FIG. 13.
Figure 15A:
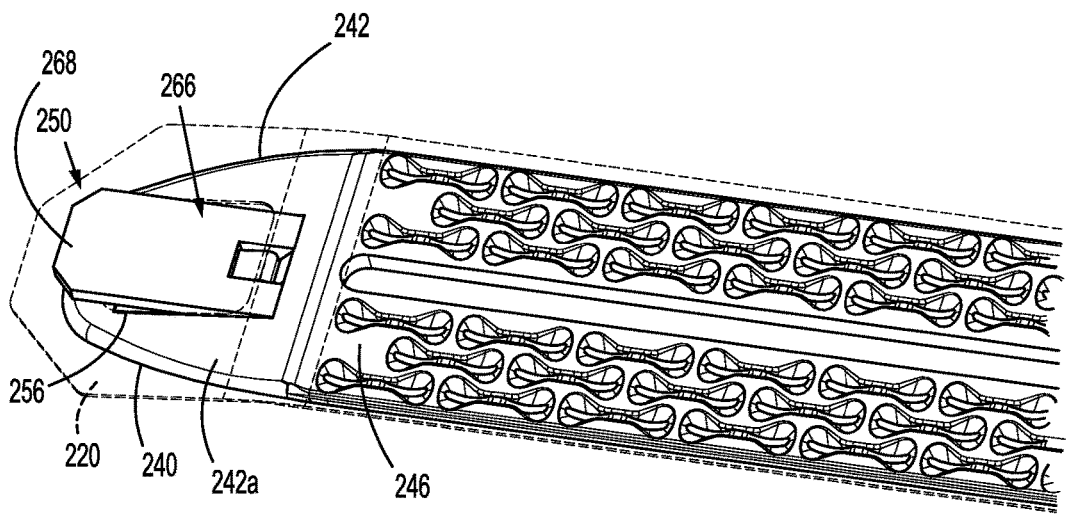
FIGS. 15A and 15B are bottom and top views, respectively, of the anvil hook of FIG. 14 in a loaded position, with the anvil buttress and the anvil assembly shown in phantom.
Figure 15B:
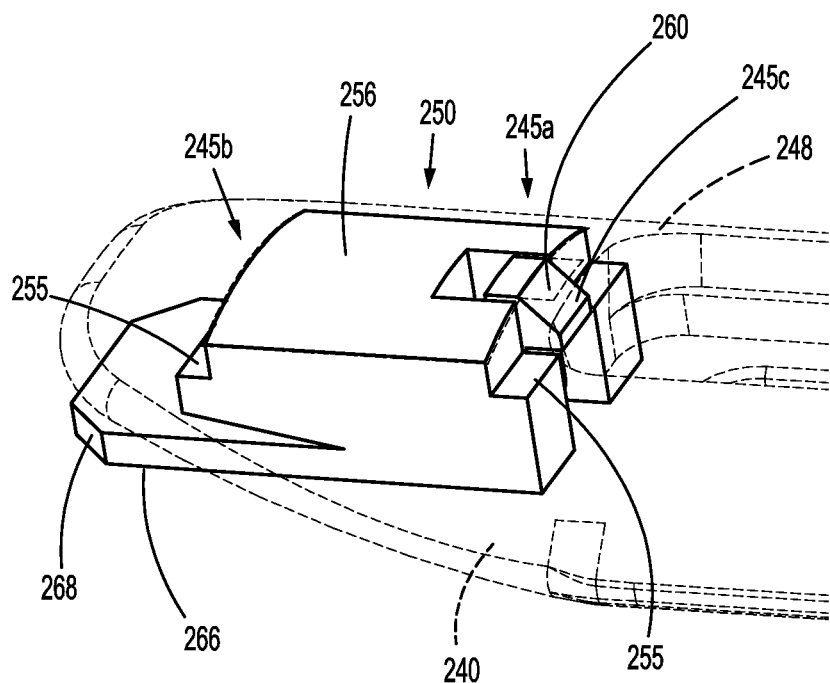
Figure 16:
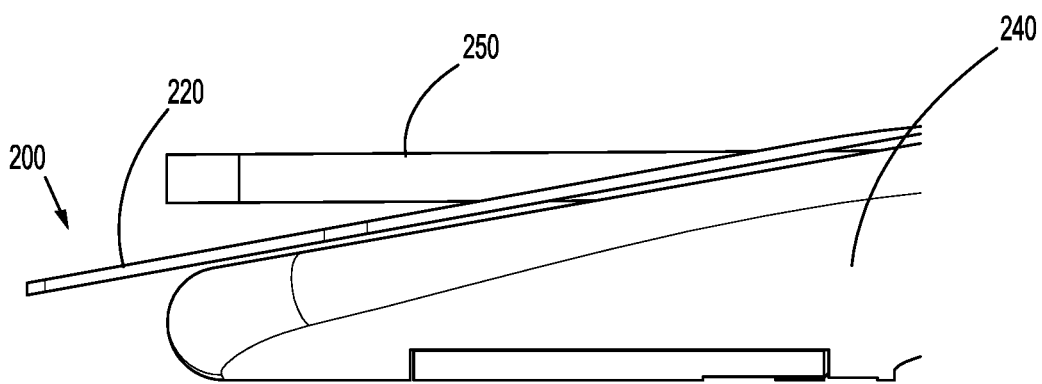
FIG. 16 is a close-up view of a distal portion of the anvil assembly with the anvil hook disposed in the loaded position and retaining the anvil buttress against the anvil assembly.

In a method of loading the anvil buttress 220 onto the anvil assembly 240, the body portion 222 of the anvil buttress 220 is positioned adjacent to the tissue facing surface 246 of the anvil assembly 240 with the cutout 223 of the anvil buttress 220 aligned with the opening 245 defined through the anvil assembly 240, as shown in FIG. 13. As seen in FIG. 14, the anvil hook 250 is then aligned with the anvil assembly 240 with the raised tier 256 facing the anvil buttress 220. The anvil hook 250 is pushed through the cutout 223 of the anvil buttress 220 and into the opening 245 of the anvil assembly 240 until the raised tier 256 is aligned with an outer surface 248 of the anvil assembly 240 and the platform 266 of the anvil hook 250 extends over the anvil buttress 220 and the distal portion 242a of the anvil plate 242, as shown in FIGS. 15A and 15B. As the anvil hook 250 is pushed into the opening 245 of the anvil plate 242, the arm 260 engages or snaps into a cavity 245c of the anvil plate 242 defined in the proximal end 245a of the opening 245, the base surface 255 engages the anvil plate 242 on the proximal and distal ends 245a, 245b of the opening 245, and the lip 268 of the platform 266 is positioned against the anvil buttress 220 and the distal portion 242a of the anvil assembly 240 thereby securing the anvil hook 250 and the anvil buttress 220 to the anvil assembly 240. As shown in FIG. 16, with the anvil hook 250 in the loaded position within the anvil assembly 240, the anvil buttress 220 is loaded and the surgical stapling apparatus 1 is ready for use.

After the surgical stapling apparatus 1 is fired and the surgical buttress assembly 200 is stapled to tissue, the anvil hook 250 is removed from the loading unit 230 by pressing the arm 260 of the anvil hook 250 distally into the cavity 256a defined in the raised tier 256 and pushing the raised surface 257 towards the staple cartridge assembly 60 to pop the anvil hook 250 out of the anvil assembly 240. In an aspect, additional or replacement reload assemblies 31 including the pre-loaded cartridge buttress 110 may be secured to the loading unit 230, as needed or desired, and the anvil buttress 220 may be secured to the loading unit 230, as described above.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

While several aspects of the disclosure have been shown in the drawings, it is not intended that the disclosure be limited thereto, as it is intended that the disclosure be as broad in scope as the art will allow and that the specification be read likewise. It is to be understood, therefore, that this disclosure is not limited to the precise aspects described, and that various other changes and modifications may be effected by one skilled in the art without departing from the scope or spirit of this disclosure. Additionally, the elements and features shown and described in connection with certain aspects may be combined with the elements and features of certain other aspects without departing from the scope of this disclosure, and that such modifications and variation are also included within the scope of this disclosure. Therefore, the above description should not be construed as limiting, but merely as exemplifications of preferred embodiments or aspects. Thus the scope of the aspects should be determined by the appended claims and their legal equivalents, rather than by the examples given.

What is claimed is:

1. A loading unit comprising:
   a staple cartridge assembly;
   an anvil assembly having an opening defined therethrough; and
   an anvil hook assembly including an anvil hook disposed within the opening of the anvil assembly and a pivot pin extending through the anvil hook and the anvil assembly such that the anvil hook is pivotable with respect to the anvil assembly about the pivot pin between a loading position and a loaded position.

2. The loading unit according to claim 1, wherein the opening of the anvil assembly is defined in a distal portion of an anvil plate.

3. The loading unit according to claim 1, wherein the anvil hook includes a body disposed within the opening of the anvil assembly and an arm extending from the body through a side of the opening open to a tissue facing surface of the anvil assembly.

4. The loading unit according to claim 3, wherein, in the loading position, the arm is disposed at a first angle with respect to the tissue facing surface of the anvil assembly and in the loaded position, the arm extends at a second angle with respect to the tissue facing surface of the anvil assembly.

5. The loading unit according to claim 3, further comprising:
   a surgical buttress assembly including a cartridge buttress releasably attached to the staple cartridge assembly, an anvil buttress releasably attachable to the anvil assembly by the anvil hook, and a connecting member interconnecting the cartridge and anvil buttresses.

6. The loading unit according to claim 5, wherein the anvil buttress includes a cutout defined therethrough that is aligned with the opening of the anvil assembly, the arm of the anvil hook extending through the cutout of the anvil buttress, wherein rotation of the anvil hook from the loading position to the loaded position pulls the anvil buttress distally and tensions the anvil buttress against the anvil assembly.

7. The loading unit according to claim 5, wherein the staple cartridge assembly includes a reload assembly including a staple cartridge, the cartridge buttress secured to the staple cartridge and the anvil buttress overlying the cartridge buttress and positionable against the anvil assembly.

8. The loading unit according to claim 7, wherein the connecting member of the surgical buttress assembly is releasably secured to a tissue facing surface of the staple cartridge proximal of staple pockets defined in the tissue facing surface of the staple cartridge.

9. An anvil buttress attachment assembly comprising:
an anvil assembly having an opening defined therethrough; and
an anvil hook assembly including an anvil hook disposed within the opening of the anvil assembly and a pivot pin extending through the anvil hook and the anvil assembly such that the anvil hook is pivotable with respect to the anvil assembly about the pivot pin between a loading position and a loaded position.

10. The anvil buttress attachment assembly according to claim 9, wherein the opening of the anvil assembly is defined in a distal portion of an anvil plate.

11. The anvil buttress attachment assembly according to claim 9, wherein the anvil hook includes a body disposed within the opening of the anvil assembly and an arm extending from the body through a side of the opening open to a tissue facing surface of the anvil assembly.

12. The anvil buttress attachment assembly according to claim 11, wherein, in the loading position, the arm is disposed at a first angle with respect to the tissue facing surface of the anvil assembly and, in the loaded position, the arm extends at a second angle with respect to the tissue facing surface of the anvil assembly.

13. The anvil buttress attachment assembly according to claim 11, further comprising:
an anvil buttress releasably attachable to the anvil assembly by the anvil hook.

14. The anvil buttress attachment assembly according to claim 13, wherein the anvil buttress includes a cutout defined therethrough that is aligned with the opening defined in the anvil assembly, the arm of the anvil hook extending through the cutout of the anvil buttress, wherein rotation of the anvil hook from the loading position to the loaded position pulls the anvil buttress distally and tensions the anvil buttress against the anvil assembly.

15. The anvil buttress attachment assembly according to claim 13, further comprising a cartridge buttress coupled to the anvil buttress by a connecting member.

16. An anvil buttress attachment assembly comprising:
an anvil assembly having an opening defined therethrough; and
an anvil hook removably positionable within the opening defined in the anvil assembly, the anvil hook including a body having an arm on a proximal end of the body that is biased in a proximal position to snap into a cavity of the anvil assembly when the anvil hook is loaded into the opening, the arm deflectable in a distal direction to remove the anvil hook from the opening of the anvil assembly.

17. The anvil buttress attachment assembly according to claim 16, wherein the opening of the anvil assembly is defined in a distal portion of an anvil plate.

18. The anvil buttress attachment assembly according to claim 16, wherein the anvil hook includes a lip extending distally from the body and wherein, when the body of the anvil hook is loaded into the opening of the anvil assembly, the lip is positioned over a distal portion of the anvil assembly.

19. The anvil buttress attachment assembly according to claim 18, further comprising:
an anvil buttress releasably attachable to the anvil assembly by the anvil hook.

20. The anvil buttress attachment assembly according to claim 19, wherein the anvil buttress includes a cutout defined therethrough that is aligned with the opening defined in the anvil assembly, the lip of the anvil hook holding the anvil buttress against the anvil assembly when the anvil hook is loaded into the opening of the anvil assembly.

* * * * *